United States Patent

Cottone et al.

[11] Patent Number: 5,884,996
[45] Date of Patent: Mar. 23, 1999

[54] STERILE HANDLE COVERS

[76] Inventors: Anthony J. Cottone; Joseph R. Cottone, Sr.; Thomas E. Cottone; John M. Cottone, all of 808 Pickens Industrial Dr., Marietta, Ga. 30062

[21] Appl. No.: 678,091

[22] Filed: Jul. 11, 1996

Related U.S. Application Data

[63] Continuation of Ser. No. 678,091, Jul. 11, 1996.

[51] Int. Cl.$^6$ .................................................. F21L 15/12
[52] U.S. Cl. ........................ 362/399; 362/457; 16/111 R
[58] Field of Search ............... 16/110.5, 111 R, 16/114 R, DIG. 12, DIG. 18, DIG. 19, DIG. 24, DIG. 25; 362/399, 400, 457, 804, 33; 493/344, 446, 449

[56] References Cited

U.S. PATENT DOCUMENTS

| | | | |
|---|---|---|---|
| D. 313,670 | 1/1991 | Barron et al. | D26/113 |
| 4,559,671 | 12/1985 | Andrews et al. | 16/111 R |
| 4,605,124 | 8/1986 | Sandel et al. | 206/223 |
| 4,646,205 | 2/1987 | Schumaker | 362/804 |
| 4,795,669 | 1/1989 | Bowskill et al. | 16/111 R |
| 4,844,252 | 7/1989 | Barron et al. | 206/223 |
| 4,878,156 | 10/1989 | Hallings et al. | 362/399 |
| 4,974,288 | 12/1990 | Reasner | 16/114 R |
| 4,975,826 | 12/1990 | Bell | 16/111 R |
| 4,976,299 | 12/1990 | Bickelman | 150/155 |
| 5,036,446 | 7/1991 | Quintanilla et al. | 362/399 |
| 5,065,296 | 11/1991 | Cude | 362/399 |
| 5,156,456 | 10/1992 | Hoftman et al. | 362/400 |
| 5,347,684 | 9/1994 | Jackson | 16/111 R |
| 5,469,600 | 11/1995 | Sandel | 16/111 R |

*Primary Examiner*—Alan Cariaso
*Attorney, Agent, or Firm*—Kilpatrick Stockton LLP

[57] ABSTRACT

Disposable sterile handle covers for surgical lamps made up of a relatively thin flexible sheet bonded to and protruding through a semi-rigid resilient skirt. The skirt allows the cover to be affixed to the handle by friction alone, thus obviating the need for adhesives. The skirt also obviates the need for a baseplate on the handle and further provides insulation from the heat generated by the lamp. The cover is manufactured with a punch die which simultaneously bonds the sheet and the skirt to each other while cutting the elements into the desired shape.

13 Claims, 2 Drawing Sheets

STERILE HANDLE COVERS

CROSS-REFERENCE TO RELATED APPLICATIONS

This application is a continuation of application Ser. No. 08/678,091, filed Jul. 11, 1996, by Anthony J. Cottone et al., "STERILE HANDLE COVERS."

FIELD OF THE INVENTION

The present invention relates to disposable sterile handle covers for handles on medical or surgical equipment, particular including handle covers for surgical lamps.

BACKGROUND OF THE INVENTION

Medical equipment, particularly operating room equipment, must be kept in a sterile condition. While many surgical instruments can be removed from the operating room after each procedure to be cleaned and sterilized, large or sensitive instruments, equipment and operating room fixtures cannot be easily moved. For example, devices such as surgical lamps cannot be removed from the operating room after each procedure. These devices, however, are in constant use and must be sterilized after each procedure. The handles of the lamps are of special concern because they receive substantial use both during and between procedures. Lamp handles are typically generally cylindrical projections with a conical skirt. The conical skirt provides insulation from the heat generated by the lamp, a resting point for the hand for increased leverage when adjusting the position of the lamp and a stop to prevent the hand from sliding beyond the handle where it might contact other portions of the lamp structure.

In the past, surgical lamps have been sterilized between procedures by first spraying the device with an antiseptic solution and then covering the handles with a sterile cover. These covers are then disposed after each use. Examples of such covers include U.S. Pat. Nos. 4,976,299 issued to Bickelman and 4,605,124 issued to Sandel et al. These patents disclose disposable covers for light handles composed of a flexible plastic or rubber. The covers are molded to conform closely to the handle, including the conical skirt.

One difficulty associated with such covers is that they are typically held in place with adhesives. After repeated uses, however, the handle becomes unusable due to the buildup of adhesive residue and must be replaced. Alternatively, the cover may be made to closely conform to the shape of the handle and so as to be held in place by friction. In order to remain securely attached, however, the cover must so closely conform to the handle that application and removal of the cover may be difficult. Also, the conical skirt portion of the handle, while providing insulation and leverage, provides an additional surface for contamination, thus increasing the complexity of the disinfecting process. If the circular skirt portion were eliminated, however, the skirt portion of a typical disposable cover would be too thin and flexible to provide the desired insulation, leverage and hand stop functions. Furthermore, disposable covers are typically made of relatively non-resilient materials and, as such, may only be used on handles of a particular size. Because handles come in a variety of sizes, a variety of different sized handle covers must be provided. This increases the manufacturing cost of such covers, as different molds must be made for each size of handle cover. Hospital procedures are also complicated by the need to track and maintain inventory of multiple cover sizes.

Alternatively, the entire handle may be disposed of and replaced after each use, as disclosed in U.S. Pat. No. 4,974,288 issued to Reasner. This approach, however, is more costly as the portion being replaced, rather than being a thin plastic cover, is instead a rigid structural element of the lamp. Furthermore, the manufacturing of such a device is more costly as it requires complex molds and molding processes.

SUMMARY OF THE INVENTION

The present invention comprises a handle cover with a flexible sheet for covering the handle and a semi-rigid skirt which eliminates the need for the conical skirt. The skirt is a disc of relatively thick resilient material with an aperture provided at its center. The aperture is of approximately the same diameter as that of a handle of a surgical lamp. Because the skirt is made of a resilient material, however, the aperture can expand to accommodate handles of different diameters. This allows the handle cover to be used on handles falling within a relatively broad range of sizes. Because a single size of cover may be used on many different handles, production and inventory costs are reduced.

A relatively thin flexible sheet or "handle cover sheet" is bonded across one side of the skirt so that the aperture is covered. Prior to bonding, the handle cover sheet is folded in such a way as to provide an excess of material at about the location of the aperture. In this manner, when the handle cover sheet is bonded to the skirt, a portion of the handle cover sheet is allowed to protrude through the aperture. Thus, when a handle is inserted through the aperture, it is completely enveloped by the handle cover sheet. The cover is retained on the handle by means of friction between the skirt and the handle. Alternatively a lip or détente may be provided on the handle and the skirt may be "snapped" over the détente.

The cover is manufactured with a punch assembly die comprising a fuser and punch die backing plate, a former handle and a punch die. The former handle protrudes from the surface of the plate. A handle cover sheet is placed over the former handle and pressed against the plate. A sheet of skirt material, with an aperture pre-cut, is placed over the handle cover sheet so that the former handle is aligned with the aperture. The punch die then presses down over the skirt material so that a portion of the handle cover sheet is pushed through the aperture by the former handle. The skirt material is pressed against the plate, trapping the remaining portion of the handle cover sheet therebetween. The punch die is provided with a cutting surface about its periphery which cuts the skirt material and the handle cover sheet to the desired shape. As the punch die presses down, the skirt and the handle cover sheet are bonded by use of an adhesive or by the application of sufficient heat and pressure to fuse the two materials together.

Accordingly, it is an object of the present invention to provide a sterile disposable handle cover for use with surgical lamps.

Another object of the invention is to provide a sterile disposable handle cover that can be used on handles of varied size.

Another object of the present invention to provide a sterile disposable handle cover for use with surgical lamps which includes a semi-rigid skirt for providing leverage in the absence of a permanent handle base portion.

Another object of the present invention to provide a sterile disposable handle cover for use with surgical lamps which includes a semi-rigid skirt for providing insulation from the heat generated by the lamp.

Another object of the present invention to provide a method for manufacturing sterile disposable handle covers for use with surgical lamps from inexpensive materials.

Other objects, features and advantages of the present invention will become apparent with reference to the remainder of the written portion and the drawings of this application.

DETAILED DESCRIPTION OF THE DRAWINGS

Figure 1:
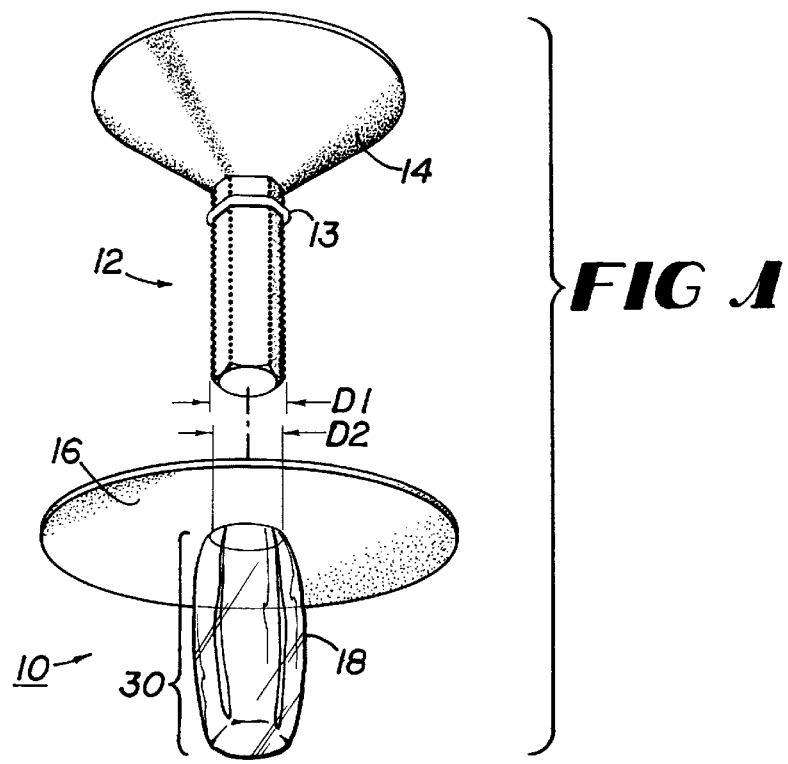
FIG. 1 is a perspective view of the cover of the present invention prior to installation on a lamp handle.

FIG. 1 illustrates an embodiment of a handle cover 10 of the present invention. Cover 10 is adapted to mount on lamp handle 12, which may or may not have a conical skirt 14. Cover 10 comprises a skirt 16 and handle cover sheet 18.

Figure 2:
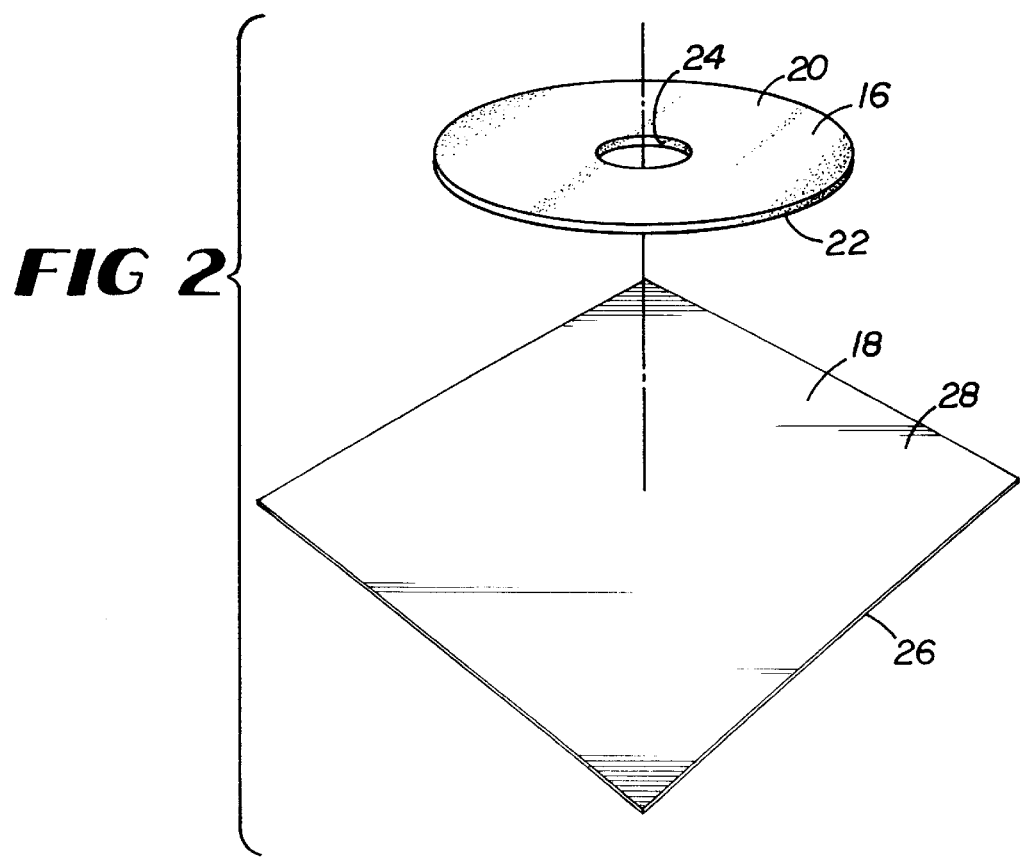
FIG. 2 is an exploded perspective view of the cover of the present invention.

Referring to FIG. 2, skirt 16 is a relatively thick disc of semi-rigid, but resilient, material having a top surface 20, a bottom surface 22 and central aperture 24. Aperture 24 may be of a diameter equal to or slightly smaller than that of handle 12. Skirt 16 is preferably at least semi-rigid. The diameter of skirt 16 should be sufficiently large so that when the handle 12 is used to manipulate the lamp, the hand of the user does not contact any uncovered portion of the lamp or handle 12. It is also important that the material of skirt 16 be sufficiently resilient to provide a frictional bond between cover 10 and handle 12. In the illustrative embodiment, cross-linked, closed cell polyethylene foam is used; however, other materials may be used for skirt 16. For instance, coated cardboard or pressboard may be used. Skirt 16 should also be of sufficient thickness to provide insulation from heat generated by a lamp. In the illustrative embodiment, where polyethylene foam is used, a thickness of approximately one quarter of an inch is appropriate, however different materials will require different thicknesses in order to provide the same degree of insulation.

Sheet 18 is a swatch of relatively thin flexible material having a bottom surface 26 and a top surface 28. Sheet 18 is a made of a relatively thin flexible material. In the illustrative embodiment, polyethylene one to five thousandths of an inch thick may be used. Other thicknesses as well as other materials, such as latex or other plastics, may also be used.

Referring to FIG. 1, top surface 28 of sheet 18 is bonded to bottom surface 22 of skirt 16 with handle cover portion 30 of sheet 18 protruding through aperture 24. Portion 30 is proportioned so that a substantial portion of handle 12 can pass through aperture 24 without puncturing sheet 18. In other words, after being inserted through aperture 24, handle 12 is enveloped by sheet 18.

Various means may be used to hold cover 10 in place. For instance, the diameter of aperture 24 may be slightly smaller than the diameter of a handle 12, and, because skirt 16 is made of a resilient material, skirt 16 will firmly "grip" handle 12 and thereby be held in place. Another advantage of the resilience of skirt 16 is that aperture 24 may expand to accommodate handles of different diameters. Thus, cover 10 may be used in conjunction with different handles having a relatively broad range of diameters without the need to provide a different skirt 16 for every type of handle. The size of aperture 24 is selected so that, given the resilience and expandability of the material, most, if not all, typical handles may be accommodated therethrough. This reduces manufacturing costs, as only one size of die for cutting skirt 16 is needed. Furthermore, cover 10 is simpler to use, as there is no longer a need to keep track of a number of different sized covers for the variety of handles that may be present in a single location.

Alternatively, handle 12 may include a retaining feature 13 which may be a circumferential lip, annular ring, protrusion or region of larger diameter. Other forms of retaining features include a détente or a region of smaller diameter located on handle 12. In either case, skirt 16 may be "snapped" over the lip or seated in the détente and thereby held in place.

Figure 3:
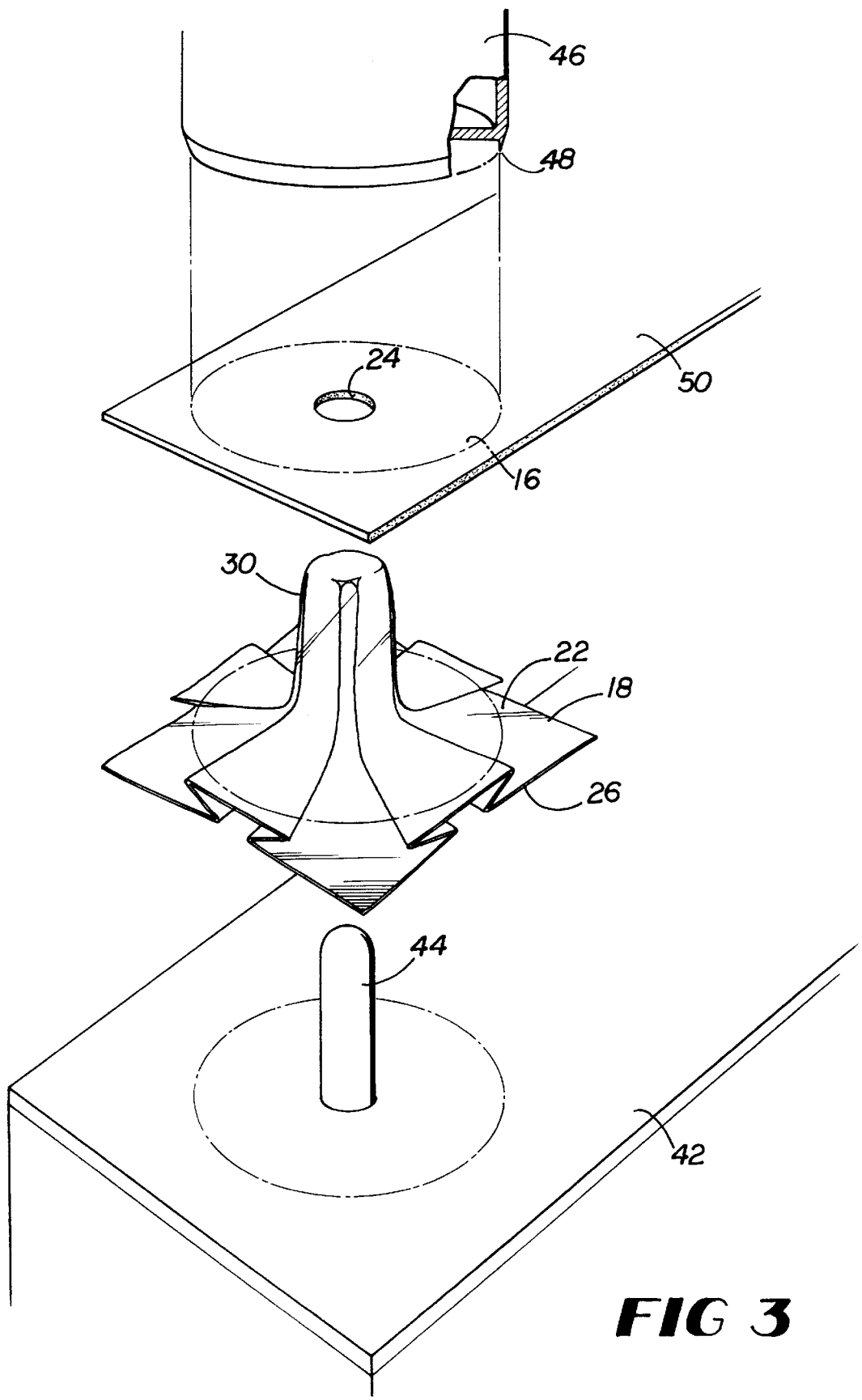
FIG. 3 is a perspective view of the cover of the present invention prior to assembly, including elements of the apparatus for assembly thereof

FIG. 3 illustrates an apparatus for manufacturing handle cover 10. Punch die assembly 40 comprises fuser and punch die backing plate 42, handle former 44 and punch die 46. Handle former 44 protrudes from the surface of plate 42 and is a cylinder of about the same dimensions as handle 12. Punch die 46 comprises circular cutting edge 48 and a central aperture (not visible) through which handle former 44 may protrude when the die assembly 40 is closed.

To form handle cover 10, sheet 18 is placed over handle former 44 and is gathered or folded so that sheet 18 generally conforms thereto. In other words, a portion of bottom surface 26 of sheet 18 is in contact with plate 42 and the remaining portion is in contact with handle former 44, creating handle cover portion 30. Sheet 18 may be folded, as illustrated in FIG. 3, or may simply be pressed over handle former 44 allowing random creases to form.

Skirt 16 is formed from skirt stock 50, a sheet of material large enough to cut skirt 16 therefrom. Aperture 24 may be pre-cut in skirt stock 50, in which case skirt stock 50 is placed over sheet 18 so that aperture 24 is aligned with handle former 44. Skirt stock 50 is then pressed down, trapping sheet 18 between it and plate 42. Handle former 44 protrudes upwards through aperture 24 and is enveloped by sheet 18. Punch die 46 is then lowered over the assembly and pressed against plate 42. As punch die 46 is pressed down, cutting surface 48 cuts through skirt stock 50 and sheet 18, thereby forming skirt 16 and conforming the outer edge of sheet 18 thereto. Alternatively, skirt 16 and aperture 16 may be cut simultaneously or sequentially before sheet 18 is inserted partially through aperture 24 or bonded to skirt 16.

When punch die 46 is closed, sheet 18 and skirt 16 are bonded together. The bonding may be accomplished by applying an adhesive to bottom surface 22 of skirt 16 (or to top surface 28 of sheet 18) prior to assembly.

Alternatively, heat may be applied to the materials when they are pressed together, thereby fusing them together. If heat fusing is selected, the temperature and pressure used should be selected to melt sheet 18 and skirt 16 sufficiently to fuse the two together without compromising the integrity of the materials. The selection of temperature and pressure is driven by a number of variables, including the material and thickness of sheet 18, the material and thickness of skirt 16, and the desire to minimize the time required to assemble the cover. Depending on the materials and thicknesses selected for the components, simple experimentation will determine the optimum temperatures and pressures used to fuse the elements together.

It is important to select materials for sheet 18 and skirt 16 that are compatible. For instance, if skirt 16 and sheet 18 are to be fused together with heat, the material selected must have complimentary melting points. In the illustrative embodiment, skirt 16 is made up of a polyethylene foam and sheet 18 is a polyethylene film. These materials have complimentary melting points and are thus well suited for heat fusing. If adhesives are used, both materials must be compatible with the selected adhesive.

Although the foregoing is provided for purposes of illustrating, explaining and describing embodiments of the present invention, modifications and adaptations to these embodiments will be apparent to those skilled in the art and may be made without departing from the scope or spirit of the invention.

We claim:

1. A cover for use on a handle affixed to a surgical lamp comprising:
   a) a resilient skirt of a thickness sufficient to insulate a user from heat generated by the lamp having a bottom surface and a central aperture defined therethrough; and
   b) a flexible sheet having a peripheral region bonded to the bottom surface and a central region which protrudes through the central aperture and is folded to conform to the handle.

2. The handle cover of claim 1 in which the skirt is cross-linked, closed-cell polyethylene foam.

3. The handle cover of claim 1 in which the skirt is cardboard.

4. The handle cover of claim 1 in which the skirt is pressboard.

5. The handle cover of claim 1 in which the flexible sheet is polyethylene film.

6. The handle cover of claim 2 in which the skirt is about one-quarter of an inch thick.

7. The handle cover of claim 5 in which the flexible sheet is about one to five thousandths of an inch thick.

8. A sterile disposable cover for a generally cylindrical handle affixed to a lamp having a diameter comprising:

a) a disc-shaped skirt made of cross-linked closed cell polyethylene foam, the skirt having a bottom surface and a central aperture in which the diameter of the central aperture is slightly less than the diameter of the handle, in which the skirt is of sufficient diameter to prevent contact between a hand and the lamp when positioning of the lamp is being adjusted and in which the skirt is about one-quarter of an inch thick; and
   b) a sheet made of polyethylene film of about one to five mils in thickness bonded to bottom surface of the skirt and covering the central aperture in such a manner as to allow a sufficient portion of the film to protrude through the central aperture so that when the handle is inserted within the aperture, the entire length of the handle can protrude therethrough without puncturing the film in which the film is folded to conform to the handle.

9. A cover for use on a handle affixed to a surgical lamp comprising:
   a) a skirt having a bottom surface and a central aperture defined therethrough in which the skirt is sufficiently resilient to allow the aperture to expand to accommodate handles with different diameters; and
   b) a flexible sheet having a peripheral region bonded to the bottom surface and a central region which protrudes through the central aperture to conform to the handle.

10. The handle cover of claim 9 in which the skirt is cross-linked, closed-cell polyethylene foam.

11. The handle cover of claim 9 in which the flexible sheet is polyethylene film.

12. The handle cover of claim 10 in which the skirt is about one-quarter of an inch thick.

13. The handle cover of claim 11 in which the flexible sheet is about one to five thousandths of an inch thick.

* * * * *